United States Patent [19]
Anton et al.

[11] Patent Number: 5,538,875
[45] Date of Patent: Jul. 23, 1996

[54] **PROCESS FOR THE PREPARATION OF PYRUVIC ACID USING PERMEABILIZED TRANSFORMANTS OF *H. POLYMORHA* AND *P. PASTORIS* WHICH EXPRESS GLYCOLATE OXIDASE AND CATALASE**

[75] Inventors: David L. Anton; Robert Dicosimo; Vincent G. Witterholt, all of Wilmington, Del.

[73] Assignee: E. I. Du Pont de Nemours and Company, Wilmington, Del.

[21] Appl. No.: 493,446

[22] Filed: Jun. 22, 1995

Related U.S. Application Data

[63] Continuation-in-part of Ser. No. 253,829, Jun. 3, 1994, abandoned, which is a continuation of Ser. No. 82,879, Jun. 25, 1993, abandoned.

[51] Int. Cl.$^6$ .................................. C12P 7/40; C12N 1/14
[52] U.S. Cl. .................. 435/136; 435/254.23; 435/255.6
[58] Field of Search ........................ 435/42, 136, 254.23, 435/255.6

[56] References Cited

PUBLICATIONS

Emes et al, Int. J. Biochem. 16:1373–1378 (1984).

*Primary Examiner*—Michael G. Wtyshyn
*Assistant Examiner*—S. Saucier

[57] ABSTRACT

A process for the production of pyruvic acid involving the enzymatic reaction of L-lactic acid and oxygen in an aqueous solution in the presence of catalysts glycolate oxidase ((S)-2-hydroxy-acid oxidase, EC 1.1.3.15) and catalase (EC 1.11.1.6). High yields of pyruvate at high purity can be achieved at commercially acceptable concentration without substantial product inhibition of the enzyme.

10 Claims, No Drawings

PROCESS FOR THE PREPARATION OF PYRUVIC ACID USING PERMEABILIZED TRANSFORMANTS OF H. POLYMORHA AND P. PASTORIS WHICH EXPRESS GLYCOLATE OXIDASE AND CATALASE

CROSS-REFERENCE TO RELATED APPLICATIONS

This is a continuation-in-part of application Ser. No. 08/253,829 filed Jun. 3, 1994, now abandoned, which is a continuation of application Ser. No. 08/082,879 filed Jun. 25, 1993, both now abandoned.

BACKGROUND OF THE INVENTION

1. Field of the Invention

This invention relates to a process for the production of pyruvic acid, where L-lactic acid and oxygen are reacted in an aqueous solution in the presence of a permeabilized whole cell catalyst which contains the enzymes glycolate oxidase ((S)-2-hydroxy-acid oxidase, EC 1.1.3.15) and catalase (EC 1.11.1.6).

2. Description of the Related Art

Pyruvic acid has been prepared by the fermentation of various carbon sources (e.g., glucose, yeast extracts and peptone), but these methods usually produce pyruvic acid in low yields (based on added carbon source) and in relatively low concentrations as one component of a mixture of fermentation products. Separation and isolation of pyruvic acid from such complex fermentation broths are generally difficult and expensive to perform.

The preparation of pyruvic acid via the microbiological oxidation of optically pure D(−)-lactic acid has been described by Cooper (U.S. Pat. No. 4,900,668; Feb. 13, 1990). Although this process improves upon other fermentation routes by not utilizing the D-lactic acid as a carbon source to produce the cell mass necessary for the reaction, a growth medium containing a second carbon source (e.g., D(−)-mannitol and corn steep liquor) are required for both the production of cell mass as well as the fermentative conversion of D-lactic acid. Additionally, D-lactic acid is not as ubiquitous in nature, and is much more expensive to produce or purchase, than L(+)-lactic acid.

The conversion of L-lactic acid to pyruvic acid has been demonstrated using the enzyme L-lactate oxidase (L-lactate: oxygen oxidoreductase, non-decarboxylating, EC 1.1.3.2) as catalyst (B. A. Burdick and J. R. Schaeffer Biotech. Lett., Vol. 9, 253–258 (1987)). L-lactate oxidase (from Pediococcus) catalyzes the oxidation of L-lactate by oxygen to pyruvate and hydrogen peroxide:

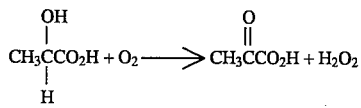

The L-lactate oxidase was co-immobilized with catalase (oxidase:catalase=1:281 (IU/IU)) to limit oxidation of pyruvate by by product hydrogen peroxide, which produces acetate and carbon dioxide. The oxidation of 0.049M solutions of L-lactate in 0.1M phosphate buffer at pH 7 resulted in yields of pyruvic acid (isolated as the 2,4-dinitrophenylhydrazone derivative) of from 0% to 47% (from 0.0M to 0.023M pyruvic acid); reusing the co-immobilized lactate oxidase/catalase catalyst in a second oxidation reaction resulted in significantly lower yields of pyruvic acid than were obtained in the first reaction.

Glycolate oxidase ((S)-2-hydroxy-acid oxidase, EC 1.1.3.15), an enzyme commonly found in leafy green plants and mammalian cells, catalyzes the oxidation of glycolic acid to glyoxylic acid. This same enzyme also catalyzes the oxidation of L-lactic acid to pyruvic acid, with the concomitant production of hydrogen peroxide. C. O. Clagett, N. E. Tolbert and R. H. Burris, J. Biol. Chem., Vol. 178, 977–987 (1949) first reported an α-hydroxy acid oxidase, extracted from a variety of green leafy plants, which catalyzed the oxidation of glycolic acid, and was also specific for the L-isomer of lactic acid. The pH optimum for the oxidation of 80 mM dl-lactate was 7.6; no reaction products were identified or isolated. N. E. Tolbert et al., J. Biol. Chem., Vol. 181, 905–914 (1949) employed a purified α-hydroxy acid oxidase from tobacco leaves for the oxidation of ca. 113 mM dl-lactic acid in phosphate buffer at pH 8; an unreported quantity of pyruvic acid was isolated from the reaction as a 2,4-dinitrophenylhydrazone, and a significant amount of carbon dioxide was also produced, indicating that a significant amount of pyruvate had reacted with co-product hydrogen peroxide to produce acetate and carbon dioxide. K. E. Richardson and N. E. Tolbert, J. Biol. Chem., Vol. 236, 1280–1284 (1961) later reported that this α-hydroxy acid oxidase was more commonly referred to as glycolic acid oxidase (i.e., glycolate oxidase).

I. Zelitch and S. Ochoa, J. Biol. Chem., Vol. 201, 707–718 (1953) reported that glycolic acid oxidase catalyzes the oxidation of L-lactic acid by molecular oxygen to produce pyruvic acid and hydrogen peroxide, and that in the absence of catalase, the peroxide reacts non-enzymatically with pyruvate to form acetate, $CO_2$, and water. Flavin mononucleotide (FMN) was identified as a required enzyme cofactor, and the addition of FMN to aqueous solutions of the enzyme greatly increased the stability of glycolic acid oxidase. The oxidation of 3.3 mM solutions of L-lactate in 50 mM phosphate buffer (pH 8.0) and in the presence of an excess of added catalase produced 3.2 mM pyruvic acid (determined colorimetrically); no product was isolated.

The oxidation of lactate to pyruvate has also been demonstrated using an L-α-hydroxy acid oxidase isolated from rat kidney (M. Blanchard et. al., J. Biol. Chem., Vol. 163, 137–144 (1946)). The oxidation of a 33 mM solution of lactate in 0.167M phosphate buffer at pH 8.0 and in the presence of added excess catalase produced pyruvate in 79% yield (isolated as the 2,4-dinitrophenylhydrazone derivative).

Additional references to the oxidation of lactic acid to pyruvic acid catalyzed by soluble enzymes include: J. C. Robinson et at., J. Biol. Chem., Vol. 237, 2001–2010 (1962) (hog renal cortex L-α-hydroxy acid oxidase), P. Urban et. al., Biochemistry, Vol. 27, 7365–7371 (1988) (rat kidney L-α-hydroxy acid oxidase), D. W. Fry and K. E. Richardson, Biochim. Biophys. Acta, Vol. 568, 135–144 (1979) (human liver glycolic acid oxidase), M. J. Emes and K. H. Erismann, Int. J. Biochem., Vol. 16, 1373–1378 (1984) (Lemna minor L. glycolate oxidase), H. S. Kim and J. D. Choi, Korean Biochem. J., Vol. 20, 350–356 (1987) (spinach glycolate oxidase).

Although the enzyme-catalyzed oxidation of L-lactic acid by oxygen is well-known, a high selectivity to pyruvic acid has only been demonstrated in one experiment (I. Zelitch and S. Ochoa) where the concentration of L-lactate was 3.3 mM; this low concentration of L-lactate limited the concentration of hydrogen peroxide formed, and in the presence of an excess of catalase, also limited the reaction of hydrogen peroxide with pyruvate to produce acetate and carbon dioxide. The recovery of such a low concentration of pyruvate (ca. 3.2 mM) from an aqueous reaction mixture is impractical for an economical manufacturing process.

SUMMARY OF THE INVENTION

The present invention relates to the preparation of pyruvic acid (or a salt thereof, as explained more fully hereafter) by oxidizing L-lactic acid (or a salt thereof) with oxygen in aqueous solution by utilizing a permeabilized whole-cell catalyst containing the two enzymes glycolate oxidase ((S)-2-hydroxy-acid oxidase, EC 1.1.3.15) and catalase (EC 1.11.1.6). Thus, the present invention provides an improved process for the production of pyruvic acid comprising the steps of reacting, at a pH of from 6 to 10, in an aqueous solution, L-lactic acid at an initial concentration of from 0.25M to 2.0M and oxygen in the presence of the permeabilized whole-cell catalyst containing the enzymes glycolate oxidase and the enzyme catalase for a time sufficient to convert the L-lactic acid to pyruvic acid in high yield and then recovering the pyruvic acid. It should be appreciated that for purposes of this invention the use of the terms pyruvic acid and L-lactic acid, particularly when referring to an aqueous solution at pH range of 6 to 10, more specifically refer to a highly dissociated state wherein a partially neutralized acid solution is predominantly present as the pyruvate ion and the L-lactate ion, respectively. Pyruvic acid is useful as a chemical intermediate in the preparation of free chemicals, agrochemicals and pharmaceuticals. Therefore, it should be further appreciated that for purposes of this invention, the reference to high yields and recovery of pyruvic acid are intended to include as equivalent a process wherein the pyruvic acid is inherently produced as an intermediate to an otherwise useful derivative compound of pyruvic acid at correspondingly high yields.

According to the present invention, pyruvic acid has been prepared via the enzyme-catalyzed oxidation of L-lactic acid with selectivities of up to 99%, and isolated in 96% yield (98% purity, sodium salt). The high initial concentration of L-lactic acid employed might have been expected to result in substrate inhibition of the glycolate oxidase, which would have limited the reaction rate and/or the final concentration of product. Similarly, a high concentration of pyruvic acid would have been expected to result in product inhibition of the enzyme, again limiting the concentration of product obtained. It was unexpected that concentrations of pyruvic acid of greater than 0.25M (greater than 22 g/L of reaction volume) could be produced under the reaction conditions employed (and described below) when one considers the well-known instability of pyruvic acid under these same reaction conditions.

Further according to the present invention, it has been discovered that yields of pyruvate as high as 99% can be obtained in unbuffered reactions run with no pH control, which is contrary to the preferred conditions for stability of pyruvic acid in aqueous solution (as described by R. W. Von Korff, Methods in Enzymology, Vol. XIII, 519–523 (1969)). All previous examples of enzymatic oxidations of L-lactate have been performed using a buffer, usually phosphate buffer. The high yields of pyruvate obtained in the present invention in the absence of buffer equal or exceed those obtained in the presence of added buffer. The preparation of pyruvate in the absence of added buffer allows for a simple isolation of product from a reaction mixture; the catalyst is removed by filtration or centrifugation, leaving an aqueous solution of a pyruvic acid salt that is easily recovered by removal of the water (for example, by stripping of water under reduced pressure, by lyophilization, or the like).

Pyruvic acid has previously been difficult to prepare in aqueous solution at concentrations of up to 1.0M because it is unstable in aqueous solution, particularly at alkaline pH, and dimerizes via an aldol condensation to produce 4-methyl-4-hydroxy-2-oxoglutarate, which can itself further polymerize [see (a) R. W. Von Korff, Methods in Enzymology, Vol. XIII, 519–523 (1969), and (b) F. D. Klinger and W. Ebertz, Ullmann's Encyclopedia of Industrial Chemistry, 5th Ed., Vol. A18, 313–319, (1991)]. The polymerization of pyruvate in aqueous solution is catalyzed by base, and is autocatalytic because as dimerization increases the pH of the solution becomes more alkaline, leading to increasing rates of dimerization and polymerization. It is for this reason that buffered solutions of pyruvate at neutral pH are reported to be more stable than unbuffered solutions, and the greatest stability of aqueous solutions of pyruvic acid in water is obtained in acidic solutions frozen at −20° C. (Von Korff). The presence of amines, bases, or various metal ions are also known to promote the dimerization of pyruvic acid in aqueous solution. The problem of production of pyruvic acid via the method described in the present invention is made more difficult by the rapid reaction of pyruvic acid with hydrogen peroxide, a co-product of the oxidation of L-lactate by oxygen (I. Zelitch and S. Ochoa (1953)).

The use of genetically-engineered, permeabilized whole-cell catalysts (i.e., a microbial transformant containing both glycolate oxidase and catalase) in the oxidation of L-lactate to pyruvate is demonstrated herein for the first time. The use of these whole-cell catalysts in the present invention provide a number of advantages over the use of soluble enzymes as catalysts. The solutions of the invention containing whole-cell catalyst can be sparged with oxygen or an oxygen-containing gas, which increases the reaction rate. Sparging a reaction mixture containing soluble enzymes results in the rapid, irreversible denaturation of glycolate oxidase, therefore sparging of reaction mixtures which use the soluble glycolate oxidase cannot be performed. At the conclusion of the reaction, the whole-cell catalyst is easily recovered for reuse by filtration or centrifugation, while the soluble enzymes cannot be centrifuged out, and filtration results in the loss of much of the soluble glycolate oxidase activity. The recovery of reusable enzyme activities for the whole-cell catalysts is extremely high after each catalyst recycle (see Examples 16 and 17), while the measured activity of remaining soluble glycolate oxidase after only one reaction is typically 20% to 60% even when no sparging of oxygen is employed.

Table 1 provides a comparison of the results obtained from the oxidation of 0.50M L-lactate solutions using a) soluble glycolate oxidase (g.o.) and soluble catalase (Comparative Example A), b) *Hansenula polymorpha* permeabilized-cell catalyst (Example 8), and c) *Pichia pastoris* pemeabilized-cell catalyst (Examples 3 and 14):

| catalyst | g.o. (IU/mL) | catalase (IU/mL) | reaction time (h) | pyruvate (%) | acetate (%) | lactate (%) |
|---|---|---|---|---|---|---|
| soluble enzymes | 6.0 | 10,000 | 5 | 95.3 | 4.5 | 0.9 |
| H. polymorpha | 6.4 | 5,000 | 2 | 97.0 | 2.5 | 0.4 |
| Pichia pastoris | 6.5 | 10,100 | 5 | 99.0 | 0.7 | 0.4 |
| Pichia pastoris | 0.5 | 2,230 | 24 | 93.7 | 1.5 | 4.9 |

The yield of pyruvate is higher, and the production of byproduct acetate is lower, when using the *P. pastoris* permeabilized whole-cell catalyst with the same concentrations of enzymes as when using soluble glycolate oxidase and catalase as catalyst. When using the *H. polymorpha* permeabilized-cell catalyst at the same glycolate oxidase concentration as for the soluble enzyme experiment, more pyruvate and less acetate (produced by the reaction of byproduct hydrogen peroxide with pyruvate) is formed, even though the concentration of endogenous cellular catalase present in the reaction mixture is half of that in the soluble enzyme reaction. When a *P. pastoris* permeabilized cell catalyst is used under the same reaction conditions, but with less than 10% the glycolate oxidase activity and only 25% of the catalase activity of the soluble enzymes example, a comparable yield of pyruvate is obtained. Lowering the concentration of glycolate oxidase or catalase in the soluble enzyme reactions results in significantly lower yields of pyruvate (see accompanying comparative Examples).

The improvement in pyruvate yields when using the permeabilized whole cell catalysts becomes even more marked as the initial concentration of L-lactate is increased above 0.50M (Table 2, ca. 0.75M L-lactate, data from Comparative Example D and Example 12):

TABLE 2

| catalyst | L-lactate (M) | catalase (IU/ml) | reaction time (h) | pyruvate (%) | acetate (%) | lactate (%) |
|---|---|---|---|---|---|---|
| soluble enzymes | 0.75 | 14,000 | 48 | 79.6 | 3.8 | 20.2 |
| Pichia pastoris (permeabilized cell) | 0.71 | 9,400 | 4 | 97.7 | 1.3 | 2.7 |

Even though the concentration of catalase in the soluble enzyme reaction is ca. 50% greater than that of the *P. pastoris* permeabilized whole-cell catalyst reaction, the permeabilized whole-cell catalyst produces 18% more pyruvate, and the reaction is complete in ca. one-tenth the time. As the L-lactate concentration is increased further to 1.0M, the yield of pyruvate that can be obtained using the permeabilized whole-cell catalyst is typically as high as 94%; these yields cannot be achieved with the soluble enzymes as catalyst, nor can the soluble enzymes be easily recovered for reuse in a subsequent reaction. Considering the reported instability of pyruvic acid under the present reaction conditions, it was not expected that a concentration of pyruvic acid approaching 1.0M could be achieved.

An additional unexpected result was obtained when one compares the results of Examples 1, 2, and 3, where three identical reactions were run using the *P. pastoris* permeabilized whole-cell catalyst. The reactions were run using either a phosphate or bicine buffer, or with no added buffer, and the yields of pyruvate were 97.6%, 93.1% and 99.0% respectively. The fact that the yield of pyruvate in the absence of added buffer was at least as great as the yield in the presence of phosphate or bicine buffer is exactly the opposite result that was predicted, based on the previous reference to the increased stability of pyruvic acid in buffered aqueous solutions compared to unbuffered solutions (Von Korff, 1969).

These results, and those in the accompanying Examples, demonstrate the unexpected improvement in pyruvate yields when using permeabilized-cell transformants as catalysts.

DESCRIPTION OF THE PREFERRED EMBODIMENTS

The catalytic oxidation of L-lactic acid or a suitable salt thereof is conveniently carried out by contacting the L-lactic acid with a source of molecular oxygen in the presence of an enzyme catalyst which catalyzes the reaction of L-lactic acid with $O_2$ to form pyruvic acid. One such catalyst is the enzyme glycolate oxidase (EC 1.1.3.15), also known as glycolic acid oxidase. Glycolate oxidase may be isolated from numerous sources well-known to the art (supra). The glycolate oxidase used in the reaction should be present in an effective concentration, usually a concentration of about 0.01 to about 1000 IU/mL, preferably about 0.1 to about 10 IU/mL. An IU (International Unit) is defined as the amount of enzyme that will catalyze the transformation of one micromole of substrate per minute. A procedure for the assay of this enzyme is found in I. Zelitch and S. Ochoa, J. Biol. Chem., Vol. 201, 707–718 (1953). This method is also used to assay the activity of recovered or recycled glycolate oxidase.

Optimal results in the use of glycolate oxidase as a catalyst for the oxidative conversion of L-lactic acid to pyruvic acid are obtained by incorporating into the reaction solution a catalyst for the decomposition of hydrogen peroxide. One such peroxide-destroying catalyst which is effective in combination with glycolate oxidase is the enzyme catalase (E.G. 1.11.1.6). Catalase catalyzes the decomposition of hydrogen peroxide to water and oxygen, and it is believed to improve yields of pyruvic acid in the present process by accelerating the decomposition of the hydrogen peroxide produced along with pyruvic acid in the glycolate oxidase-catalyzed reaction of lactic acid with $O_2$. The concentration of catalase should be 500 to 50,000 IU/mL preferably 2,000 to 15,000 IU/mL. It is preferred that the catalase and glycolate oxidase concentrations be adjusted within the above ranges so that the ratio (measured in IU for each enzyme) of catalase to glycolate oxidase is at least about 250:1.

In addition to using soluble enzymes as comparisons, microbial transformants which express glycolate oxidase activity as well as endogenous catalase activity have been prepared, and their use as a microbial catalyst in the present invention demonstrated. A microbial cell catalyst which has been utilized in the present invention is a transformant of *Hansenula polymorpha* (a methylotrophic yeast). Several transformants of *H. polymorpha* having sufficient glycolate oxidase activity have been prepared by inserting the DNA for glycolate oxidase into an expression vector under the control of the formate dehydrogenase (FMD) promoter. *H. polymorpha* was transformed with this vector and a strain producing high levels of glycolate oxidase was selected and designated *H. polymorpha* GO1 (deposited on Mar. 30, 1993 ARS Patent Culture Collection, under the Northern Regional Research Laboratory accession number: Y-21065, with the Northern Regional Research Laboratories International Depository Authority, 1815 N. University Street, Peoria, Ill. 61604).

*H. polymorpha* cell catalysts were typically prepared by first growing an inoculum of an *H. polymorpha* transformant in 500 mL of YPD (Difco), pH 4.4. This culture was then inoculated into a fermenter containing 10 L of Yeast Nitrogen Base (YNB, Difco) without amino acids (14 g), ammonium sulfate (50 g) and methanol (100 g), at pH 5.0. The fermenter was operated for 42.5 hours at 37° C., an agitation rate of 400 rpm, constant pH of 5.0, 40% dissolved oxygen (controlled), and 14 psig of air. At the conclusion of the fermentation, 1.0 kg of glycerol was added and the cells harvested by centrifugation, frozen in liquid nitrogen, and stored at −80° C.

A second microbial cell catalyst which has been utilized in the present invention is a transform ant of *Pichia pastoris* (a methylotrophic yeast) which expresses the glycolate oxidase enzyme from spinach, as well as an endogenous catalase. Several transformants of *P. pastoris* having sufficient glycolate oxidase activity have been prepared by inserting a DNA fragment containing the spinach glycolate oxidase gene into a *P. pastoris* expression vector (pHIL-D4) such as to be under control of the methanol inducible alcohol oxidase I promoter, generating the plasmid pMP1. *P. pastoris* strain GTS115 (NRRL Y-15851) was transformed by plasmid pMP1 and a selection was done as to allow integration of the linearized plasmid pMP1 into the chromosomal alcohol oxidase I locus and replacement of alcohol oxidase gene with glycolate oxidase gene. A pool of such transformants were next selected for maximal number of integrated copies of the expression cassette. A high copy number transformant was isolated and designated *P. pastoris* strain GS115-MSP10 (deposited on Sep. 24, 1992 in ARS Patent Culture Collection, under the Northern Regional Research Laboratory accession number: Y-21001, with the Northern Regional Research Laboratories International Depository Authority, 1815 N. University Street, Peoria, Ill. 61604).

*P. pastoris* cells were typically prepared by growing an inoculum in 100 mL of YNB containing 1% glycerol. After 48 hours growth at 30° C., the cells were transferred into a fermenter containing 10 L of media composed of yeast nitrogen base (YNB) without amino acids (134 g), glycerol (100 g), and biotin (20 mg). The fermentation was operated at pH 5.0 (controlled with $NH_4OH$), 30° C., agitation rate of 200 rpm, aeration of 5 slpm, 5 psig of air, and dissolved oxygen maintained at no lower than 50% saturation. When glycerol was depleted, the cells were induced to express glycolate oxidase by growth in the same media except that methanol (50 g) was substituted for glycerol. Glycolate oxidase activity during induction was followed by enzyme assay. After 24 hours of induction the cells were harvested following treatment with glycerol (1 kg). Following harvest the cells were frozen in liquid nitrogen and stored at −80° C.

*H. polymorpha* and *P. pastoris* cell transformants required permeabilization prior to use as catalyst for the oxidation of glycolic acid to glyoxylic acid. A variety of known methods of permeabilization were useful for preparing cells with sufficient glycolate oxidase activity (see Felix, H., Anal. Biochemistry, Vol. 120, 211–234,(1982)). Typically, a suspension of 10 wt % wet cells in 0.1% (v/v) "TRITON" X-100/20 mM phosphate buffer (pH 7.0) was mixed for 15 minutes, then frozen in liquid nitrogen, thawed, and washed with 20 mM phosphate/0.1 mM FMN buffer (pH 7.0). A second method of permeabilization was performed by mixing a suspension of 10 wt % wet cells in 0.1% (w/v) benzalkonium chloride/20 mM phosphate buffer (pH 7.0) for 60 minutes, then washing the permeabilized cells with 20 mM phosphate/0.1 mM FMN buffer (pH 7.0). Once permeabilized, the amount of whole cell catalyst added to a reaction mixture was chosen so as to provide the necessary concentrations of glycolate oxidase and catalase activities as described above for the corresponding soluble enzymes. Recoveries of glycolate oxidase and catalase activities of greater than 100% of their initial values are due to increased permeabilization of the cells during the course of the reaction.

Microbial cell transformants were assayed for glycolate oxidase activity by accurately weighing ca. 5–10 mg of wet cells (blotted on filter paper to remove excess moisture) into a 3-mL quartz cuvette containing a magnetic stirring bar, then adding 2.0 mL of a solution which was 0.12 mM in 2,6-dichlorophenol-indophenol (DCIP) and 80 mM in TRIS (tris(hydroxymethyl)aminomethane) buffer (pH 8.3). The cuvette was capped with a rubber septum and the solution deoxygenated by bubbling with nitrogen for 5 minutes. To the cuvette was then added by syringe 40 mL of 1.0M glycolic acid/1.0M TRIS (pH 8.3), and the mixture stirred while measuring the change in absorption with time at 605 nm ($\epsilon$=22,000). Catalase activity was assayed by accurately weighing ca. 2–5 mg of wet cells (blotted on filter paper to remove excess moisture) into a 3-mL quartz cuvette containing a magnetic stirring bar, then adding 2.0 mL of 17 mM phosphate buffer (pH 7.0) and 1.0 mL of 59 mM hydrogen peroxide in 17 mM phosphate buffer (pH 7.0) and measuring the change in absorption with time at 240 nm ($\epsilon$=39.4). Glycolate oxidase and catalase activities of the *H. polymorpha* or *P. pastoris* wet cells (permeabilized) cultured in different media ranged from 20 to 120 DCIP IU/gram wet cells for glycolate oxidase and 30,000 to 200,000 IU/gram wet cells for endogenous catalase.

An optional but sometimes beneficial ingredient in the reaction solution is flavin mononucleotide (FMN), which may be added at a concentration of up to about 2.0 mM, preferably up to about 0.2 mM. It is believed the FMN increases the productivity of the glycolate oxidase, by which is meant the amount of glycolic acid converted to glyoxylic acid per unit of enzyme. It is to be understood that the concentration of added FMN is in addition to any PMN present with the enzyme, because FMN is often also added to the soluble enzyme during the preparation of the soluble enzyme. The structure of FMN and a method for its analysis is found in K Yagai, Methods of Biochemical Analysis, Vol. X, Interscience Publishers, New York, 1962, p. 319–355.

L-lactic acid is available commercially. In the process of the invention its initial concentration is in the range of 0.25M to 2.0M, preferably between 0.25M and 1.0M. It can be employed in the reaction as the acid, or as a compatible salt thereof; that is, a salt that is water-soluble and whose cation does not interfere with the desired conversion of L-lactic acid to pyruvic acid. Suitable and compatible salt-forming cationic groups are readily determined by trial. Representative of such salts are the alkali metal, alkaline earth metal, ammonium, substituted ammonium, phosphonium, and substituted phosphonium salts. L-lactic acid produced via fermentation can be used as substrate as a filtered solution directly from the fermenter, without purification or isolation from the fermentation broth.

The conversion of L-lactic acid to pyruvic acid is conveniently and preferably conducted in aqueous media. The pH of the reaction mixture is adjusted to a value between 6 and 10, preferably between 7 and 9. Within this pH range, the exact value may be adjusted to obtain the desired pH by adding any compatible, non-interfering base, including (but not limited to) alkali metal hydroxides, carbonates, bicarbonates and phosphates. The pH of an unbuffered reaction mixture decreases by ca. 2 pH units as the reaction proceeds, so it is often preferred to start the reaction near the high end of the maximum enzyme activity pH range, about 9.0–8.5, and allow it to drop during the reaction; typically, the final pH of unbuffered reaction mixtures ranges from ca. 6.7 to 7.5. The pH can optionally be maintained by the separate addition of a non-interfering inorganic or organic buffer which has some buffering capacity around the pH of 7.5, since the optimal enzyme activity for the oxidation of L-lactate is close to this value; an initial pH of 7.5 is employed when using a suitable buffer. It is understood that L-lactic and pyruvic acid are highly dissociated in water, and that at a pH of between 7 and 10 are largely if not substantially present as L-lactate and pyruvate ions.

Oxygen ($O_2$), the oxidant for the conversion of L-lactic acid to pyruvic acid, may be added as a gas to the reaction by agitation of the liquid at the gas-liquid interface or through a membrane permeable to oxygen. When employing permeabilized whole-cell catalyst, oxygen may be added by sparging (bubbling) oxygen or an oxygen containing gas through the reaction mixture. Under most conditions, the reaction rate is at least partially controlled by the rate at which oxygen can be dissolved into the aqueous medium. Thus, although oxygen can be added to the reaction as air, a relatively pure form of oxygen may also be used. Although no upper limit of oxygen pressure is known, oxygen pressures up to 50 atmospheres may be used, and an upper limit of 15 atmospheres is preferred. Agitation is important to maintaining a high oxygen dissolution (hence reaction) rate. Any convenient form of agitation is useful, such as stirring or sparging. High shear agitation or agitation that produces foam may decrease the activity of the permeabilized cell catalysts, and should be avoided.

The reaction temperature is an important variable, in that it affects reaction rate and the stability of the enzymes. Typically a reaction temperature of up to about 40° C. may be used without substantial loss of catalytic activity, while the preferred reaction temperature range is from about 0° C. to about 15° C. Operating in the preferred temperature range maximizes recovered enzyme activity at the end of the reaction. The temperature should not be so low that the aqueous solution starts to freeze. Temperature can be controlled by ordinary methods, such as, but not limited to, by using a jacketed reaction vessel and passing liquid of the appropriate temperature through the jacket. The reaction vessel may be constructed of any material that is inert to the reaction ingredients.

Upon completion of the reaction, permeabilized cell catalysts may be separated from reaction mixtures for recycle by centrifugation or filtration. Following the removal of the microbial cell catalyst, flavin mononucleotide (FMN) which may have been added is removed by contacting the solution with activated carbon. The desired pyruvic acid (i.e., the pyruvic acid and pyruvate salts) can then be recovered as the solution, per se, or the resulting solution can be concentrated and the pyruvic acid recovered by removal of water; again for example, by stripping of water under reduced pressure, lyophilization (freeze drying) or any other method as generally known in the art.

In the following examples, which serve to further illustrate the invention, the yields of pyruvate and acetate, and the recovered yield of L-lactate, are percentages based on the total amount of L-lactic acid present at the beginning of the reaction, unless otherwise indicated. Analyses of reaction mixtures were performed using high pressure liquid chromatography (HPLC): organic acid analyses were performed using a Bio-Rad HPX-87H column.

Comparative Example A (Using Soluble Enzymes)

Into a 3 oz. Fischer-Porter glass aerosol reaction vessel was placed a magnetic stirring bar and 10 mL of an aqueous solution containing sodium L-lactate (0.500M), isobutyric acid (HPLC internal standard, 0.100M), soluble spinach glycolate oxidase (6.0 IU/mL), and soluble *Aspergillus niger* catalase (10,000 IU/mL) at pH 9.0 (adjusted with 50% NaOH) and at 15° C.; no buffer was added. The reaction vessel was sealed and the reaction mixture was cooled to 15° C., then the vessel was flushed with oxygen by pressurizing to 70 psig and venting to atmospheric pressure five times with stirring. The vessel was then pressurized to 70 psig of oxygen and the mixture stirred at 15° C. Aliquots (0.10 mL) were removed by syringe through a sampling port (without loss of pressure in the vessel) at regular intervals for analysis by HPLC to monitor the progress of the reaction. After 5 hours, the HPLC yields of pyruvate and acetate were 95.3% and 0.9%, respectively, and 4.5% lactate remained. The remaining activities of glycolate oxidase and catalase were 68% and 100%, respectively, of their initial values.

Comparative Example B (Using Soluble Enzymes)

The procedure described in Comparative Example A was repeated using a 10 mL aqueous solution containing sodium L-lactate (0.500M), isobutyric acid (HPLC internal standard, 0.100M), soluble spinach glycolate oxidase (2.0 IU/mL), and soluble *Aspergillus niger* catalase (20,000 IU/mL) at pH 9.0 (adjusted with 50% NaOH), and the reaction run at 15° C; no buffer was added. After 7 hours, the HPLC yields of pyruvate and acetate were 91.6% and 0.6%, respectively, and 7.1% lactate remained. The remaining activities of glycolate oxidase and catalase were 21% and 100%, respectively, of their initial values.

Comparative Example C (Using Soluble Enzymes)

The procedure described in Comparative Example A was repeated using a 10 mL aqueous solution containing L-lactic acid (96% L-isomer, 4% D-isomer, 0.500M), $KH_2PO_4$ (0.50M), FMN (0.01 mM), isobutyric acid (HPLC internal standard, 0.100M), soluble spinach glycolate oxidase (2.0 IU/mL), and soluble *Aspergillus niger* catalase (14,000

IU/mL) at pH 8.3 (adjusted with 50% NaOH), and the reaction run at 5° C. After 18 hours, the HPLC yields of pyruvate and acetate were 90.5% and 4.2%, respectively, and 6.4% lactate remained. The remaining activities of glycolate oxidase and catalase were 57% and 100%, respectively, of their initial values.

Comparative Example D (Using Soluble Enzymes)

The procedure described in Comparative Example A was repeated using a 10 mL aqueous solution containing L-lactic acid (96% L-isomer, 4% D-isomer, 0.750M total), $KH_2PO_4$ (0.750M), FMN (0.01 mM), isobutyric acid (HPLC internal standard, 0.100M), soluble spinach glycolate oxidase (1.0 IU/mL), and soluble *Aspergillus niger* catalase (14,000 IU/mL) at pH 8.1 (adjusted with 50% NaOH) and at 5° C. After 48 hours, the HPLC yields of pyruvate and acetate were 79.6% and 3.8%, respectively, and 20.2% lactate remained. The remaining activities of glycolate oxidase and catalase after 18 hours of reaction were 22% and 100%, respectively, of their initial values.

Comparative Example E (Using Soluble Enzymes)

The procedure described in Comparative Example A was repeated using a 10 mL aqueous solution containing lithium L-lactate (0.750M), FMN (0.01 mM), isobutyfic acid (HPLC internal standard, 0.100M), bicine buffer (0.788M), soluble spinach glycolate oxidase (1.0 IU/mL), and soluble *Aspergillus niger* catalase (1,400 IU/mL) at pH 8.9 (adjusted with 50% NaOH) and the reaction run at 5° C. After 28.5 hours, the HPLC yields of pyruvate and acetate were 47.7% and 43.6%, respectively, and 11.5% lactate remained. The remaining activity of glycolate oxidase and catalase were 40% and 100%, respectively, of their initial values.

Comparative Example F (Using Soluble Enzymes)

The procedure described in Comparative Example A was repeated using a 10 mL aqueous solution containing lithium L-lactate (0.750M), FMN (0.01 mM), isobutyric acid (HPLC internal standard, 0.100M), ethylenediamine (0.788M), soluble spinach glycolate oxidase (1.0 IU/mL), and soluble *Aspergillus niger* catalase (1,400 IU/mL) at pH 7.5 (adjusted with 50% NaOH) and the reaction run at 5° C. After 40 hours, the HPLC yields of pyruvate and acetate were 33.2% and 0%, respectively, and 22.2% lactate remained. The remaining activity of glycolate oxidase and catalase were 28% and 100%, respectively, of their initial values.

Comparative Example G (Using Soluble Enzymes)

The procedure described in Comparative Example A was repeated using a 10 mL aqueous solution containing L-lactic acid (96% L-isomer, 4% D-isomer, 0.750M total), FMN (0.01 mM), isobutyric acid (HPLC internal standard, 0.100M), Tris buffer (0.750M), soluble spinach glycolate oxidase (1.0 IU/mL), and soluble *Aspergillus niger* catalase (1,400 IU/mL) at pH 8.3 (adjusted with 50% NaOH) and the reaction run at 5° C. After 39 hours, the HPLC yields of pyruvate and acetate were 55.1% and 6.3%, respectively, and 2.7% lactate remained. The remaining activity of glycolate oxidase and catalase were 29% and 94%, respectively, of their initial values.

EXAMPLE 1

Into a 3 oz. Fischer-Porter glass aerosol reaction vessel was placed a magnetic stirring bar and 10 mL of an aqueous solution containing sodium L-lactate (0.500M), $KH_2PO_4$ (0.50M), and isobutyric acid (HPLC internal standard, 0.100M) at pH 9.0 (adjusted with 50% NaOH), and the solution cooled to 5° C. To the vessel was then added 0.75 g (wet weight) of *Pichia pastoris* transformant GS115-MSP10 (6.52 IU/mL glycolate oxidase and 10,100 IU/mL catalase) which had been permeabilized by treatment with 0.1% benzalkonium chloride ("BARQUAT" OJ-50), then the reaction vessel was sealed and the reaction mixture was cooled to 5° C. The vessel was flushed with oxygen by pressurizing to 70 psig and venting to atmospheric pressure five times with stirring, then the vessel was pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 5 hours, the HPLC yields of pyruvate and acetate were 97.6% and 2.5%, respectively, and 0.3% lactate remained. The remaining permeabilized cell activity of glycolate oxidase and catalase were 104% and 105%, respectively, of their initial values.

EXAMPLE 2

The reaction in Example 1 was repeated using bicine buffer (0.5M) in place of $KH_2PO_4$ (0.50M). After 5 hours, the HPLC yields of pyruvate and acetate were 93.1% and 6.3%, respectively, and 0.4% lactate remained. The remaining permeabilized cell activity of glycolate oxidase and catalase were 107% and 122%, respectively, of their initial values.

EXAMPLE 3

The procedure described in Example 1 was repeated using 10 mL of an aqueous solution containing sodium L-lactate (0.500M) and isobutyric acid (HPLC internal standard, 0.100M) at pH 9.0 (adjusted with 50% NaOH), to which was added 0.75 g (wet weight) of *Pichia pastoris* transformant GS115-MSP 10 (6.52 IU/mL glycolate oxidase and 10,100 IU/mL catalase) which had been permeabilized by treatment with 0.1% benzalkonium chloride ("BARQUAT" OJ-50); no buffer was added. After 5 hours, the HPLC yields of pyruvate and acetate were 99.0% and 0.7%, respectively, and 0.4% lactate remained. The remaining permeabilized cell activity of glycolate oxidase and catalase were 119% and 113%, respectively, of their initial values.

EXAMPLE 4

The procedure described in Example 1 was repeated using 10 mL of an aqueous solution containing sodium L-lactate (0.500M) and isobutyric acid (HPLC internal standard, 0.100M) at pH 9.0 (adjusted with 50% NaOH), to which was added 0.35 g (wet weight) of *Pichia pastoris* transformant GS115-MSP10 (2.26 IU/mL glycolate oxidase and 5,000 IU/mL catalase) which had been permeabilized by treatment with 0.1% benzalkonium chloride ("BARQUAT" OJ-50); no buffer was added. After 8 hours, the HPLC yields of pyruvate and acetate were 97.4% and 2.3%, respectively, and 0.4% lactate remained. The remaining permeabilized cell activity of glycolate oxidase and catalase were 123% and 150%, respectively, of their initial values.

EXAMPLE 5

The procedure described in Example 1 was repeated using 10 mL of an aqueous solution containing sodium L-lactate (0.500M) and isobutyric acid (HPLC internal standard, 0.100M) at pH 9.0 (adjusted with 50% NaOH), to which was added 0.18 g (wet weight) of *Pichia pastoris* transformant GS115-MSP 10 (1.13 IU/mL glycolate oxidase and 2,500 IU/mL catalase) which had been permeabilized by treatment with 0.1% benzalkonium chloride ("BARQUAT" OJ-50); no buffer was added. After 10 hours, the HPLC yields of pyruvate and acetate were 92.9% and 5.0%, respectively, and 3.3% lactate remained. The remaining permeabilized cell activity of glycolate oxidase and catalase were 121% and 228%, respectively, of their initial values.

EXAMPLE 6

The procedure described in Example 1 was repeated using 10 mL of an aqueous solution containing sodium L-lactate (1.00M) and isobutyric acid (HPLC internal standard, 0.100M) at pH 9.0 (adjusted with 50% NaOH), to which was added 0.71 g (wet weight) of *Pichia pastoris* transformant GS115-MSP10 (4.59 IU/mL glycolate oxidase and 10,000 IU/mL catalase) which had been permeabilized by treatment with 0.1% benzalkonium chloride ("BARQUAT" OJ-50); no buffer was added. After 8 hours, the HPLC yields of pyruvate and acetate were 89.1% and 8.4%, respectively, and 1.3% lactate remained. The remaining permeabilized cell activity of glycolate oxidase and catalase were 124% and 145%, respectively, of their initial values.

EXAMPLE 7

The procedure described in Example 1 was repeated using 10 mL of an aqueous solution containing sodium L-lactate (0.50M) and isobutyric acid (HPLC internal standard, 0.100M) at pH 9.0 (adjusted with 50% NaOH), to which was added 0.66 g (wet weight) of *Pichia pastoris* transformant GS115-MSP10 (6.27 IU/mL glycolate oxidase and 10,000 IU/mL catalase) which had been permeabilized by treatment with 0.1% benzalkonium chloride ("BARQUAT" OJ-50); no buffer was added. The reaction temperature was 15° C. and the oxygen pressure was 70 psig. After 3 hours, the HPLC yields of pyruvate and acetate were 98.2% and 1.2%, respectively, and 0.6% lactate remained. The remaining permeabilized cell activity of glycolate oxidase and catalase were 124% and 130%, respectively, of their initial values.

EXAMPLE 8

The procedure described in Example 7 was repeated using 10 mL of an aqueous solution containing sodium L-lactate (0.50M) and isobutyric acid (HPLC internal standard, 0.100M) at pH 9.0 (adjusted with 50% NaOH), to which was added 1.04 g (wet weight) of *Hansenula polymorpha* transformant GO1 (6.47 IU/mL glycolate oxidase and 5,000 IU/mL catalase) which had been permeabilized by treatment with 0.1% benzalkonium chloride ("BARQUAT" OJ-50); no buffer was added. The reaction temperature was 15° C. and the oxygen pressure was 70 psig. After 2 hours, the HPLC yields of pyruvate and acetate were 97.0% and 2.5%, respectively, and 0.4% lactate remained. The remaining permeabilized cell activity of glycolate oxidase and catalase were 99% and 155%, respectively, of their initial values.

EXAMPLE 9

The reaction described in Example 7 was repeated at 5° C. and 120 psig of oxygen. After 4 hours, the HPLC yields of pyruvate and acetate were 93.1% and 3.7%, respectively, and 2.2% lactate remained. The remaining permeabilized cell activity of glycolate oxidase and catalase were 66% and 180%, respectively, of their initial values.

EXAMPLE 10

The reaction described in Example 7 was repeated at 30° C. and 70 psig of oxygen. After 3 hours, the HPLC yields of pyruvate and acetate were 89.9% and 6.5%, respectively, and 0.6% lactate remained. The remaining permeabilized cell activity of glycolate oxidase and catalase were 45% and 140%, respectively, of their initial values.

EXAMPLE 11

A 300-mL EZE-Seal stirred autoclave reactor equipped with Dispersimax Impeller (Autoclave Engineers) was charged with 100 mL of a solution containing sodium L-lactate (5.50 g, 0.50M). To the reactor was then added 6.70 g (wet weight) of *Pichia pastoris* transformant strain GS115-MSP10 (6.70 IU/mL glycolate oxidase and 11,770 IU/mL catalase) which had been permeabilized by treatment with 0.1% benzalkonium chloride ("BARQUAT" MB-50), and the mixture adjusted to pH 9.0 with 50% NaOH and cooled to 5° C. The reactor purged with oxygen, then the mixture was stirred at 750 rpm, which bubbled oxygen through the mixture via the action of the turbine impeller, and at 5° C. under 40 psig of oxygen. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC using 0.10M isobutyfic acid added to the sample as internal standard. After 3.0 hours, the HPLC yields of pyruvate and acetate were 99.2% and 1.4%, respectively, and 0.6% lactate remained. The recovered activities of permeabilized-cell glycolate oxidase and catalase were 107% and 106% of their initial values, respectively.

The reaction mixture was centrifuged to remove the permeabilized-cell catalyst, and the resulting supernatant filtered through a 0.2 mm nylon filter. The pH of the resulting filtrate was adjusted to 4.6 with 1.0N HCl, then the solution was frozen and the water removed by lyophilization to produce 5.20 g of sodium pyruvate (96% isolated yield, 98% sodium pyruvate as determined by HPLC analysis).

EXAMPLE 12

The procedure described in Example 11 was repeated using 100 mL of an aqueous solution containing sodium L-lactate (0.713M) at pH 7.5 (adjusted with 50% NaOH), to which was added 5.00 g (wet weight) of *Pichia pastoris* transformant GS115-MSP10 (3.27 IU/mL glycolate oxidase and 10,200 IU/mL catalase) which had been permeabilized by treatment with 0.1% benzalkonium chloride ("BARQUAT" MB-50); no buffer was added. The reaction temperature was 5° C. and the oxygen pressure was 70 psig. After 4 hours, the HPLC yields of pyruvate and acetate were 97.7% and 1.3%, respectively, and 2.7% lactate remained. The remaining permeabilized cell activity of glycolate oxidase and catalase were 111% and 100%, respectively, of their initial values.

EXAMPLE 13

The procedure described in Example 11 was repeated using 100 mL of an aqueous solution containing sodium L-lactate (1.06M) at pH 7.5 (adjusted with 50% NaOH), to which was added 5.00 g (wet weight) of *Pichia pastoris* transformant GS115-MSP 10 (6.25 IU/mL glycolate oxidase and 17,400 IU/mL catalase) which had been permeabilized by treatment with 0.1% benzalkonium chloride ("BARQUAT" MB-50); no buffer was added. The reaction temperature was 5° C. and the oxygen pressure was 70 psig. After 5 hours, the HPLC yields of pyruvate and acetate were 92.9% and 3.3%, respectively, and 4.2% lactate remained. The remaining permeabilized cell activity of glycolate oxidase and catalase were 101% and 83%, respectively, of their initial values.

EXAMPLE 14

The procedure described in Example 11 was repeated using 100 mL of an aqueous solution containing sodium L-lactate (0.532M) at pH 7.4 (adjusted with 50% NaOH), to which was added only 1.04 g (wet weight) of *Pichia pastoris* transformant GS115-MSP 10 (0.52 IU/mL glycolate oxidase and 2,230 IU/mL catalase) which had been permeabilized by treatment with 0.1% benzalkonium chloride ("BARQUAT" MB-50); no buffer was added. The reaction temperature was 5° C. and the oxygen pressure was 70 psig. After 24 hours, the HPLC yields of pyruvate and acetate were 93.7% and 5.0%, respectively, and 2.8% lactate remained. The remaining permeabilized cell activity of glycolate oxidase and catalase were 79% and 43%, respectively, of their initial values.

EXAMPLE 15

The procedure described in Example 11 was repeated using 100 mL of an aqueous solution containing sodium L-lactate (1.00M) at pH 7.5 (adjusted with 50% NaOH), to which was added 4.99 g (wet weight) of *Hansenula polymorpha* transformant GO1 (4.12 IU/mL glycolate oxidase and 9,660 IU/mL catalase) which had been permeabilized by treatment with 0.1% benzalkonium chloride ("BARQUAT" MB-50); no buffer was added. The reaction temperature was 5° C. and the oxygen pressure was 70 psig. After 6 hours, the HPLC yields of pyruvate and acetate were 93.5% and 1.5%, respectively, and 4.9% lactate remained. The remaining permeabilized cell activity of glycolate oxidase and catalase were 135% and 99%, respectively, of their initial values.

EXAMPLE 16

A 300-mL EZE-Seal stirred autoclave reactor equipped with Dispersimax Impeller (Autoclave Engineers) was charged with 100 mL of a solution containing sodium lactate (1.06M), at pH 7.5, and the solution cooled to 5° C. To the reactor was then added 5.0 g (wet weight) of *Pichia pastoris* transformant strain GS115-MSP 10 ( 5.54 IU/mL glycolate oxidase and 14,400 IU/mL catalase ) which had been permeabilized by treatment with 0.1% benzalkonium chloride ("BARQUAT" MB-50), and the reactor purged with oxygen. The mixture was then stirred at 750 rpm, which bubbled oxygen through the mixture via the action of the turbine impeller, and at 5° C. under 70 psig of oxygen. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC using 0.20M isobutyric acid added to the sample as internal standard. After 5 hours, the HPLC yields of pyruvate and acetate were 95.7% and 2.5%, respectively, and 1.9% lactate remained. The remaining permeabilized cell activity of glycolate oxidase and catalase were 116% and 107% of their initial values, respectively.

The microbial cell catalyst was recovered from the reaction mixture described above by centrifugation. Without further treatment the cell pellet was mixed with 100 mL of fresh reaction mixture, and the reaction repeated. This catalyst recycle procedure was performed for five consecutive batch reactions, and the reaction time, the recovery of glycolate oxidase and catalase activity (based on the initial activity of the permeabilized cells), and yields of pyruvic, acetic, and lactic acid are listed in the table below:

| run # | time (h) | glycolate oxidase (%) | catalase (%) | pyruvate (%) | acetate (%) | lactate (%) |
|---|---|---|---|---|---|---|
| 1 | 5 | 116 | 107 | 95.7 | 2.5 | 1.9 |
| 2 | 6 | 110 | 88 | 96.0 | 4.5 | 0.8 |
| 3 | 7 | 108 | 71 | 92.3 | 5.4 | 2.4 |
| 4 | 8 | 125 | 89 | 90.7 | 7.2 | 2.1 |
| 5 | 10 | 112 | 41 | 86.1 | 10.2 | 3.7 |

EXAMPLE 17

A 300-mL EZE-Seal stirred autoclave reactor equipped with Dispersimax Impeller (Autoclave Engineers) was charged with 100 mL of a solution containing sodium lactate (0.50M), at pH 7.5, and the solution cooled to 5° C. To the reactor was then added 5.0 g (wet weight) of *Pichia pastoris* transformant strain GS115-MSP 10 ( 5.19 IU/mL glycolate oxidase and 10,800 IU/mL catalase ) which had been permeabilized by treatment with 0.1% benzalkonium chloride ("BARQUAT" MB-50), and the reactor purged with oxygen. The mixture was then stirred at 750 rpm, which bubbled oxygen through the mixture via the action of the turbine impeller, and at 5° C. under 70 psig of oxygen. The reaction was monitored by taking a 0.40 mL aliquot of the reaction mixture at regular intervals, faltering the aliquot using a Millipore Ultrafree-MC 10,000 NMWL Filter Unit, and analyzing the filtrate by HPLC using 0.20M isobutyric acid added to the sample as internal standard. After 2 hours, the HPLC yields of pyruvate and acetate were 99.3% and 0.5%, respectively, and 2.4% lactate remained. The remaining permeabilized cell activity of glycolate oxidase and catalase were 75% and 81% of their initial values, respectively.

The microbial cell catalyst was recovered from the reaction mixture described above by centrifugation. Without further treatment the cell pellet was mixed with 100 mL of fresh reaction mixture, and the reaction repeated. This catalyst recycle procedure was performed for twelve consecutive batch reactions, and the reaction time, the recovery of glycolate oxidase and catalase activity (based on the initial activity of the permeabilized cells), and yields of pyruvic, acetic, and lactic acid are listed in the table below:

| run # | time (h) | glycolate oxidase (%) | catalase (%) | pyruvate (%) | acetate (%) | lactate (%) |
|---|---|---|---|---|---|---|
| 1 | 2 | 75 | 81 | 99.3 | 0.5 | 2.4 |
| 2 | 2 | 95 | 87 | 97.9 | 0.6 | 1.5 |
| 3 | 2.5 | 93 | 69 | 95.4 | 0.4 | 3.3 |
| 4 | 2.5 | 89 | 90 | 94.6 | 1.0 | 4.4 |
| 5 | 3 | 79 | 56 | 95.4 | 0.9 | 3.7 |
| 6 | 3 | 79 | 74 | 95.7 | 1.1 | 4.9 |
| 7 | 3.5 | 76 | 58 | 94.8 | 1.0 | 4.2 |

| run # | time (h) | glycolate oxidase (%) | catalase (%) | pyruvate (%) | acetate (%) | lactate (%) |
|---|---|---|---|---|---|---|
| 8 | 3.5 | 75 | 50 | 92.6 | 1.2 | 6.2 |
| 9 | 5 | 74 | 36 | 93.9 | 1.8 | 4.3 |
| 10 | 6 | 68 | 48 | 92.2 | 2.4 | 5.4 |
| 11 | 7.5 | 74 | 26 | 90.8 | 3.0 | 6.2 |
| 12 | 7 | 58 | 24 | 87.2 | 3.9 | 9.0 |

EXAMPLE 18

A fermentation broth containing 109.9 g/L of ammonium lactate (97.8% L-lactate, 2.2% D-lactate), 0.8 g/L acetate, and 2.8 g/L maltose was centrifuged to remove particulate matter, then filtered through a 0.45 mm filter. The concentration of ammonium lactate in the resulting solution was 1.10M (117.6 g/L determined by HPLC analysis). Into a 300-mL EZE-Seal stirred autoclave reactor equipped with Dispersimax Impeller (Autoclave Engineers) was placed 45 mL of the 1.10M filtered fermentation broth, then 55 mL of distilled water was added to produce 100 mL of an aqueous solution containing 0.50M ammonium lactate. To the reactor was then added 6.70 g (wet weight) of recycled *Pichia pastoris* transformant strain GS115-MSP10 (6.66 IU/mL glycolate oxidase and 11,070 IU/mL catalase) which had been permeabilized by treatment with 0.1% benzalkonium chloride ("BARQUAT" OJ-50), and the mixture adjusted to pH 7.5 with 50% NaOH and cooled to 5° C. The reactor purged with oxygen, then the mixture was stirred at 750 rpm, which bubbled oxygen through the mixture via the action of the turbine impeller, and at 5° C. under 40 psig of oxygen. The reaction was monitored by taking a 0.40 mL aliquot of the reaction mixture at regular intervals, faltering the aliquot using a Millipore Ultrafree-MC 10,000 NMWL Filter Unit, and analyzing the filtrate by HPLC using 0.10M isobutyric acid as internal standard. After 3.0 hours, the HPLC yields of pyruvate and acetate were 94.1% (96.2% based on L-lactate) and 2.8%, respectively, and 2.5% lactate remained. The recovered activities of permeabilized-cell glycolate oxidase and catalase were 101% and 56% of their initial values, respectively.

EXAMPLE 19

Into a 14 L fermenter was placed 4.60 L of the 1.10M filtered fermentation broth described in Example 18, then 5.40 L of distilled water was added to produce 10.0 L of an aqueous solution containing 0.51M ammonium lactate, and the mixture cooled to 10° C. To the fermenter was then added 500 g (wet weight) of *Pichia pastoris* transformant strain GS115-MSP10 (2.52 IU/mL glycolate oxidase and 6,900 IU/mL catalase) which had been permeabilized by treatment with 0.1% benzalkonium chloride ("BARQUAT" MB-50), and the mixture adjusted to pH 7.5 with 50% NaOH and cooled to 10° C. The fermenter was purged with oxygen, then the mixture was stirred at 250 rpm and at 10° C. under 25 psig of oxygen while sparging the mixture with oxygen at 4.5 slpm. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC using 0.10M isobutyric acid as internal standard. After 20 hours, the HPLC yields of pyruvate and acetate were 93.0% and 5.8%, respectively, and 1.5% lactate remained. The recovered activities of permeabilized-cell glycolate oxidase and catalase were 260% and 62% of their initial values, respectively.

Having thus described and exemplified the invention with a certain degree of particularity, it should be appreciated that the following claims are not to be so limited but are to be afforded a scope commensurate with the wording of each element of the claim and equivalents thereof.

What is claimed is:

1. A process for the production of pyruvic acid comprising the steps of reacting, in an aqueous solution and at a pH of from 6 to 10 with or without a buffer, L-lactic acid at an initial concentration of from 0.25M to 2.0M and oxygen in the presence of a permeabilized whole cell catalyst selected from the group consisting of transformants of *Hansenula polymorpha* and *Pichia pastoris*, wherein the transformant expresses glycolate oxidase and catalase enzymes, to convert the L-lactic acid to pyruvic acid, and then recovering the pyruvic acid.

2. The process of claim 1 wherein said permeabilized whole cell catalyst is selected from the group consisting of the transformant *Hansenula polymorpha* GO1 deposited under NRRL No. Y-21065 and the transformant *Pichia pastoris* GS115-MSP10 deposited under NRRL No. Y-21001 wherein the transformant expresses glycolate oxidase and catalase enzymes.

3. The process of claim 1 wherein the glycolate oxidase and catalase are present in the reaction mixture at a concentration of 0.01 to 1,000 IU/mL and from 500 to 50,000 IU/mL respectively.

4. The process of claim 3 wherein the glycolate oxidase and catalase are present in the reaction mixture at a concentration of 0.1 to 10 IU/mL and 2,000 to 15,000 IU/mL respectively, and the IU/mL ratio of catalase to glycolate oxidase is at least 250:1.

5. The process of claim 1 wherein the initial concentration of L-lactic acid is from 0.25M to 1.0M.

6. The process of claim 5 wherein the glycolate oxidase and catalase are present in the reaction mixture at a concentration of 0.01 to 1,000 IU/mL and from 500 to 50,000 IU/mL, respectively.

7. The process of claim 5 wherein the glycolate oxidase and catalase are present in the reaction mixture at a concentration of 0.1 to 10 IU/mL and 2,000 to 15,000 IU/mL, respectively, and the IU/mL ratio of catalase to glycolate oxidase is at least 250:1.

8. The process of claim 1 wherein a buffer is used.

9. The process of claim 1 without a buffer.

10. The process of claim 2 without a buffer.

* * * * *